(12) United States Patent
Cai et al.

(10) Patent No.: US 11,219,369 B2
(45) Date of Patent: Jan. 11, 2022

(54) OCT PROBE USED FOR HUMAN OPEN LUMEN SYSTEM

(71) Applicant: Guangzhou Winstar Medical Technology Company Limited, Guangzhou (CN)

(72) Inventors: Zhigang Cai, Guangzhou (CN); Guanyue Kong, Guangzhou (CN); Jun Gao, Guangzhou (CN); Hongjian Ma, Guangzhou (CN); Ziyi Chen, Guangzhou (CN); Jiaoyang Li, Guangzhou (CN); Bailing Li, Guangzhou (CN)

(73) Assignee: GUANGZHOU WINSTAR MEDICAL TECHNOLOGY COMPANY LIMITED, Guangzhou (CN)

( * ) Notice: Subject to any disclaimer, the term of this patent is extended or adjusted under 35 U.S.C. 154(b) by 313 days.

(21) Appl. No.: 16/362,613

(22) Filed: Mar. 23, 2019

(65) Prior Publication Data

US 2019/0216324 A1     Jul. 18, 2019

Related U.S. Application Data

(63) Continuation of application No. PCT/CN2017/076894, filed on Mar. 16, 2017.

(30) Foreign Application Priority Data

Sep. 27, 2016 (CN) .................. 201610862276.X

(51) Int. Cl.
  *A61B 5/00* (2006.01)
  *G02B 27/00* (2006.01)

(52) U.S. Cl.
  CPC .......... *A61B 5/0066* (2013.01); *A61B 5/0073* (2013.01); *A61B 5/0084* (2013.01);
  (Continued)

(58) Field of Classification Search
  CPC ........................... A61B 5/0066; A61B 5/0073
  See application file for complete search history.

(56) References Cited

U.S. PATENT DOCUMENTS

2014/0031679 A1* 1/2014 Tashiro ................ A61B 5/0077
                                                    600/425
2014/0340756 A1* 11/2014 Sinclair .............. G02B 27/0018
                                                    359/614

(Continued)

FOREIGN PATENT DOCUMENTS

CN    103492857 A    1/2014
CN    105722445 A    6/2016
CN    106175700 A    12/2016

OTHER PUBLICATIONS

International Search Report issued in corresponding International application No. PCT/CN2017/076894, dated Jun. 26, 2017(4 pages).

*Primary Examiner* — Joseph M Santos Rodriguez

(57) ABSTRACT

The invention discloses an OCT probe used for human open lumen system, comprising a probe protector, a probe body, an oily liquid, a metal coil, a probe guard tip and a light-guided optical fiber; the probe body is match mounted will the metal coil, and the metal coil is mounted on the rear end of the probe body; the light-guided optical fiber is fixed inside the probe body; the probe guard tip is sleeved on the probe body, the probe protector is sleeved on the probe guard tip and sleeved on the metal coil; the oily liquid is filled between the probe guard tip and the probe protector, and between the metal coil and the probe protector. The (Continued)

invention effectively remedy for the defect that the image is unclear by filling the oily liquid between the probe protector and the probe body.

7 Claims, 1 Drawing Sheet

(52) U.S. Cl.
CPC .... *A61B 5/0086* (2013.01); *A61B 2562/0233* (2013.01); *G02B 27/0018* (2013.01)

(56) References Cited

U.S. PATENT DOCUMENTS

2015/0331191 A1 11/2015 Hasegawa et al.
2016/0120408 A1 5/2016 Bhagavatula et al.

\* cited by examiner

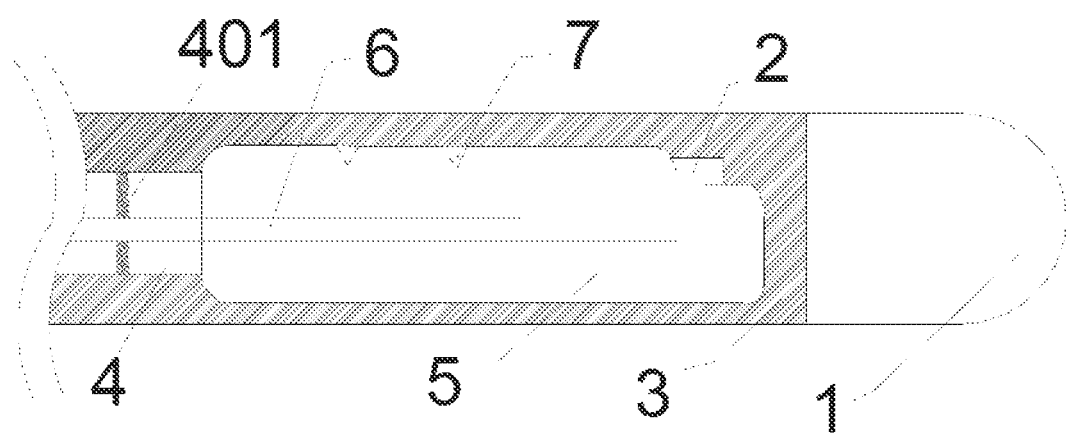

OCT PROBE USED FOR HUMAN OPEN LUMEN SYSTEM

CROSS-REFERENCE TO RELATED APPLICATIONS

This application is a continuation-application of PCT/CN2017/076894 filed with the Chinese Patent Office on 16 Mar. 2017. This application is based upon and claims the benefit of priority to Chinese Patent Application No. 201610862276.X filed with the Chinese Patent Office on 27 Sep. 2016.

TECHNICAL FIELD

The invention relates to the field of medical equipment, and more specifically to an OCT probe used for human open lumen system.

BACKGROUND

Optical coherence tomography (OCT) is a rapidly developing high-resolution imaging technique in the past decade, it's based on the principle of low-coherence interference of light and, combined with confocal microscopic technique to detect echo time-delay and echo intensity signals of the backscattered wave of the incident weak coherent light to different depth layers of biological tissue, achieving a high-resolution microstructure of the sample in two or three dimensions by scanning. In such way, a nondestructive tomographic image of the measured sample in vivo is obtained. OCT imaging technique eliminates the need for any developer, has no ionization and fluorescence effects, and is more secure than traditional imaging techniques, is known as 'optical biopsy'.

The OCT tomography scanning imaging has higher resolution than X-ray imaging, ultrasound imaging and magnetic resonance imaging. The current OCT tomography scanning imaging technique can achieve 10 µm resolution, which is two orders of magnitude higher than X-ray and magnetic resonance imaging technique. High-resolution, nondestructive testing and other advantages make OCT tomography scanning imaging technique widely used in fields such as ophthalmology, dermatology, dentistry and craft product testing, and such technique has already achieved satisfactory results.

The current OCT tomography scanning imaging technique uses near-infrared light (such as 1300 nm) as the detection source, while near-infrared light does not penetrate the red blood cells in the blood vessels well. Therefore, when applying OCT technique, in the cardiovascular field, it is necessary to block blood flow in a short time or locally flush blood vessel or take other methods to exclude blood in blood vessels, and then scan imaging.

This method of detection is risky and can easily cause myocardial ischemia in patients, and the operation is complicated, which requires very high operational skills for the operator. To widely apply OCT technique to areas such as angiography and intraluminal tissue (such as lung) testing, improving the imaging quality of OCT tomography scanning imaging technique is the key.

Currently, the OCT probe used for blood vessel detection has a defect of existing an air gap between the scanning probe and the outer protective sleeve. The presence of this air gap makes it easy for the light-spot emerging from the probe to be distorted, thereby makes the light-spot becoming an elliptical spot. This convergence effect of the beam would definitely result in a decrease in image quality. The patent CN201520036955.2 adopts a method of completely matching the inner wall of the protective sleeve with the front d of the probe body Although the problem of the air gap is solved, there is transmission relationship between protective sleeve with the probe body due to the complete matching, resulting from the fact that the OCT probe mainly uses a circumferential annular scanning method during biopsy, which requires that the OCT protection sleeve in contact with human tissue cannot perform circumferential annular motion. Therefore, it is important to find a method that can effectively improve the quality of OCT tomography scanning imaging.

SUMMARY

In order to overcome the shortage of conventional technology, the objective of the present invention is to provide an OCT probe used for human open lumen system, which can solve the defect that the image is unclear on account of the air gap between the probe body and the outer probe protector during scanning imaging.

The object of present invention is achieved by the following technical solutions:

An OCT probe used for human open lumen system, comprising: a probe protector, a probe body, an oily liquid, a metal coil, a probe guard tip and a light-guided optical fiber; wherein, the probe body is match mounted with the metal coil, and the metal coil is mounted on the rear end of the probe body; the light-guided optical fiber is fixed inside the probe body; the probe guard tip is sleeved on the probe body, the probe protector is sleeved on the probe guard tip and sleeved on the metal coil; and the oily liquid is filled between the probe guard tip and the probe protector, and between the metal coil and the probe protector.

Preferably, the OCT probe further comprising a fixing member, the fixing member is used to fix the probe body and the probe guard tip. That can further solve the technical problem of fixing the probe guard tip and the probe body.

Preferably, the probe protector is a medical round head nylon elastic tube. That can further solve the technical problem of selecting the material of the probe protector.

Preferably, the front end of the probe protector is hemispherical, and the outer diameter of the probe protector is less than or equal to 3 mm. That can further solve the technical problem of the selection of the probe protector.

Preferably, the fixing member is a medical plastic fixing member or a medical stainless steel fixing member. That can further solve the technical problem of selecting the material of the fixing member.

Preferably, the probe guard tip is a medical stainless steel guard tip. That can further solve the technical problem of selecting the material of the probe guard tip.

Preferably, the oily liquid has the same refractive index as the probe protector. That can further solve the technical problem of light guiding offset.

Preferably, the OCT probe further comprising a connecting stator, the connecting stator is used to fix the metal coil and the light-guided optical fiber. That can further solve the problem of fixing the metal coil and guided optical fiber.

Compared with the conventional technology, the beneficial effects of the present invention are:

The invention effectively remedy for the defect that the OCT probe scanning imaging technology causes the image to be unclear due to the air gap between the probe body and the outer probe protector when scanning in the open lumen system of the human body and optimize the imaging effect, by filling oily liquid between the outer probe protector and the probe body.

BRIEF DESCRIPTION OF THE DRAWINGS

FIG. 1 is a schematic view showing the structure of an OCT probe used for human open lumen system according to the present invention.

Reference numerals: 1, probe protector; 2, probe body; 3, oily liquid; 4, metal coil; 401, connecting stator; 5, probe guard tip; 6, light-guided optical fiber; 7, fixing member.

DESCRIPTION OF EMBODIMENTS

Hereinafter, the present invention will be further described in conjunction with the drawings and specific embodiments:

As shown in FIG. 1, the embodiment provides an OCT probe used for human open lumen system, comprising a probe protector 1, a probe body 2, an oily liquid 3, a metal coil 4, a fixing member 7, a connecting stator 401, a probe guard tip 5, and a light-guided optical fiber 6, the probe body 2 is match mounted with the metal coil 4, and the metal coil 4 is mounted on the rear end of the probe body 2, the light-guided optical fiber 6 is fixed inside the probe body 2, and the fragile optical fiber can be effectively protected by the probe body 2, and the connecting stator 401 is used to fix the metal coil 4 and the light-guided fiber 6. It can be rotated and translated synchronously with the light-guided optical fiber by the torque of the metal coil 4 transmitting by the connecting stator 401, so that the probe is more smoothly and smoothly used. The human open lumen system (or lumen)mentioned in this embodiment may comprises the respiratory tract, the genital tract, the anorectal tract, the esophagus, the ear canal, the urethra, the uterine cavity, the gastral cavity, the oral cavity, etc., these are merely illustrative examples and not all of the open lumen system of the human body are listed.

The probe guard tip 5 is sleeved on the probe body 2, and the probe guard tip 5 is a medical stainless steel probe guard tip. The fixing member 7 is used to fix the probe body 2 to the probe guard tip 5. The fixing member 7 is a medical plastic fixing member or a medical stainless steel fixing member. The probe protector 1 is sleeved on the probe guard tip 5 and the metal coil 4, and the probe protector 1 is a medical round nylon flexible tube. The front end of the probe protector 1 is hemispherical, and the outer diameter of the probe protector 1 is less than or equal to 3 mm and the oily liquid 3 is filled between the probe guard tip 5 and the metal coil 4 and the probe protector 1. The oily liquid 3 has the same refractive index as the probe protector 1. When they have the same or similar refractive index, the light exits will not cause the deflection of the light on account to the difference in refractive index, that will not result the circumstance of image unclear when there is no oily liquid 3, the image would be unclear. And the oily liquid has the characteristics of colorless, transparent, non-toxic, and low viscosity, which further ensures the clarity of the transmitted image.

Various other changes and modifications may be made by those skilled in the art in light of the above-described technical solutions and concepts, and all such changes and modifications are intended to fall within the scope of the appended claims.

The invention claimed is:

1. An OCT probe applied to a human open lumen, comprising: a probe protector, a probe body, an oily liquid, a metal coil, a probe guard tip and a light guide optical fiber; herein the probe body is match mounted will the metal coil, and the metal coil is mounted on the rear end of the probe body; the light guide optical fiber is fixed inside the probe body; the probe guard tip is sleeved on the probe body, the probe protector is sleeved on the probe guard tip and sleeved on the metal coil; and the oily liquid is filled between the probe guard tip and the probe protector, and between the metal coil and the probe protector;

wherein the OCT probe further comprises a connecting stator used to fix the metal coil and the light guide optical fiber together.

2. The OCT probe according to claim 1, wherein further comprising a fixing member, the fixing member is used to fix the probe body and the probe guard tip.

3. The OCT probe according to claim 2, wherein the fixing member is a medical plastic fixing member or a medical stainless steel fixing member.

4. The OCT probe according to claim 1, wherein the probe protector is a medical round head nylon elastic tube.

5. The OCT probe according to claim 1, wherein the front end of the probe protector is hemispherical, and the outer diameter of the probe protector is less than or equal to 3 mm.

6. The OCT probe according to claim 1, wherein the probe guard tip is a medical stainless steel guard tip.

7. The OCT probe according to claim 1, wherein the oily liquid has the same refractive index as the probe protector.

* * * * *